United States Patent [19]
Gertz et al.

[11] Patent Number: 5,270,365
[45] Date of Patent: Dec. 14, 1993

[54] PREVENTION AND TREATMENT OF PERIODONTAL DISEASE WITH ALENDRONATE

[75] Inventors: Barry J. Gertz, Summit, N.J.; Gideon A. Rodan, Bryn Mawr, Pa.

[73] Assignee: Merck & Co., Inc., Rahway, N.J.

[21] Appl. No.: 808,701

[22] Filed: Dec. 17, 1991

[51] Int. Cl.$^5$ .................... A61K 7/22; A61K 33/42; A61K 31/66
[52] U.S. Cl. .................... 514/108; 424/49; 424/54; 514/900; 514/902
[58] Field of Search .................... 424/49–58; 514/900–902, 105

[56] References Cited

U.S. PATENT DOCUMENTS

| | | |
|---|---|---|
| 3,429,963 | 2/1969 | Shedlovsky . |
| 3,962,432 | 6/1976 | Schmidt-Dünker . |
| 4,042,679 | 8/1977 | Gaffer . |
| 4,098,880 | 7/1978 | Gaffar . |
| 4,100,270 | 7/1978 | Gaffar . |
| 4,102,993 | 7/1978 | Gaffar . |
| 4,123,512 | 10/1978 | Gaffar . |
| 4,138,477 | 2/1979 | Gaffar . |
| 4,440,779 | 4/1984 | Doherty et al. . |
| 4,446,052 | 5/1984 | Sunberg et al. . |
| 4,621,077 | 11/1986 | Rosini et al. . |
| 4,639,338 | 1/1987 | Stahl et al. . |
| 4,677,132 | 6/1987 | Hayward . |
| 4,711,880 | 12/1987 | Stahl et al. . |
| 4,816,437 | 3/1989 | Nimberg et al. . |
| 4,877,603 | 10/1989 | Degenhardt et al. . |
| 4,973,576 | 11/1990 | Sakamoto et al. . |
| 4,990,503 | 2/1991 | Isomura et al. . |
| 5,002,937 | 3/1991 | Bosies et al. . |
| 5,019,651 | 5/1991 | Kieczykowski . |

FOREIGN PATENT DOCUMENTS

| | | |
|---|---|---|
| 8781453A | 11/1987 | Australia . |
| 0272208A1 | 6/1988 | European Pat. Off. . |
| 0274346 | 5/1989 | European Pat. Off. . |
| 0317505A1 | 5/1989 | European Pat. Off. . |
| 0320118 | 6/1989 | European Pat. Off. . |
| 0320455A1 | 6/1989 | European Pat. Off. . |
| 0449405A2 | 10/1991 | European Pat. Off. . |

OTHER PUBLICATIONS

J. Periodontol., Oct. 1992, 63(10), 825–30, Brunsvold et al., Effects of a Bisphosphonate on Experimental Periodontitis in Monkeys.

(List continued on next page.)

*Primary Examiner*—Shep Rose
*Attorney, Agent, or Firm*—Charles M. Caruso; Melvin Winokur

[57] ABSTRACT

This invention claims a method for treating periodontal disease in mammals, including humans, by administering an effective amount of 4-amino-1-hydroxybutylidene-1,1-bisphosphonic acid or a pharmaceutically acceptable salt including the monosodium salt tridydrate (alendronate) of the formula:

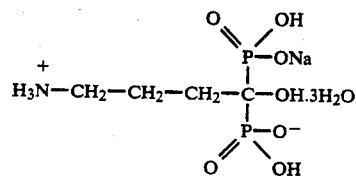

The compounds are useful in the treatment of alveolar bone loss associated with peridontitis and periodontal disease.

10 Claims, 3 Drawing Sheets

OTHER PUBLICATIONS

Clin. Ortop. & Related Research, H. Fleish, 217, 72–78 (1987).
American Journal of Anatomy, W. Beertsen et al., 174, 83–103 (1985).
Calc. Tiss. Res., A. Larsson, 16, 109–127 (1974).
Calcif. Tissue Internat., Ogawa et al., 44, 46–60 (1989).
Adv. Dental Res., J. W. Simmelink, 1, 356–365 (1987).
Infection & Immunity, Riviere et al., vol. 59 (10), 3377–3380 (1991).
Infection & Immunity, Ebersole et al., vol. 59 (10), 3351–3359 (1991).
Periodontal Disease: Recognition, Interception & Prevention, Quintessence Publishing Co., 21–23, (1984).
J. Clin. Periodontol, Haffajee et al., 10, 298–310 (1983).
Science, Holt et al., 239, 55–57, (1988).
J. Periodontal Res. Nalbandian et al., 20, 154–164 (1987).
J. Periodontal Res., Kiel et al., 18, 200–211 (1983).
J. Periodontal Res., Kornman et al., 16, 363–371 (1981).
Infection and Immunity, Manti et al., 45, 172–179 (1984).
Infection and Immunity, McArthur et al., 57, 2313–2317 (1989).
Immunol. Invest. Nisengard et al., 18, 225–237 (1989).
Infection and Immunity, Slots et al., 23, 260–269 (1979).
Infection & Immunity, Beem et al., 59 (11) 4034–4041 (1991).
Cancer, Jung A. et al., 48, 1922–1925 (1985).
J. Periodont. Res., Steffensen et al., 107–113 (1991).

FIG. 2

FIG. 3

PREVENTION AND TREATMENT OF PERIODONTAL DISEASE WITH ALENDRONATE

This invention relates to the administration of an effective amount of 4-amino-1-hydroxybutylidene-1,1-bisphosphonic acid or a pharmaceutically acceptable salt including the monosodium salt trihydrate (alendronate) to treat periodontal disease in mammals, including humans.

BACKGROUND OF THE INVENTION

Periodontal disease (Pyorrhea) involves the inflammation and degeneration of tissues that surround and support mammalian teeth. These include the gingiva, alveolar bone, periodontal ligament, and cementum. Periodontitis or the loss of supporting bone is the latest stage of this progressive disorder and is the major cause of tooth loss in adults. Juveniles also experience a form of periodontitis which results in alveolar bone loss and subsequent loss of teeth. Identified causal factors for this disease include poor hygiene which leads to buildup of bacterial plaque; malocclusion, tartar buildup, food impaction, and faulty dental restorations. The rate of osseous bone loss (resorption) depends upon the severity of the above conditions or causative factors. Symptoms of periodontitis include deepening of the gingival pockets between the gingivae and the teeth; loss of attachment of the gums to the teeth; and bone loss. Microbes proliferate in the recessed areas and accelerate disease progression. Periodontal surgery remains the primary corrective measure of this disease. Periodontal surgery (scaling and planing), however, may induce or, at a minimum, is associated with periodontal bone loss.

Antibiotics, astringent agents, and mouthwashes are not effective for long-term treatment of periodontal disease. Home care that includes brushing, rinsing, and flossing coupled with dental curettage and polishing help deter the disease. Other preventative treatments include hydrogen peroxide mouth rinses (3 percent $H_2O_2$ in warm water). Carbamide peroxide (Urea hydrogen peroxide, $CH_6N_2O_3$) is also used in the local treatment of minor infections and inflammation caused by periodontitis. Penicillin (1000–1500 milligrams daily) or erythromycin may be used if severe oral signs or symptoms are present.

An additional approach to the treatment of periodontal disease includes the use of non-steroidal anti-inflammatory agents to hinder disease progression. It is known according to U.S. Pat. No. 4,677,132 that the analgesic and anti-inflammatory agent Etodolac may also inhibit bone resorption and bone loss associated with periodontal disease. Etodolac is a substituted pyrano [3,4 b] indole derivative. U.S. Pat. No. 4,440,779 describes the use of novel tricyclic analgesic and anti-inflammatory agents useful in the treatment of fever, pain and inflammatory conditions associated with arthritis, spondylitis, gout, dysmennohrea, upper respiratory disorders, and periodontal diseases.

The use of a number of bisphosphonic acid derivatives in the treatment of a broad range of calcium metabolism disorders including periodontitis is known. Eur. Pat. App. No. -320-455-A discloses the use of N-aralkyl-amino-1-hydroxyalkane-1,1-diphosphonic derivatives as useful in the treatment of inflammatory/degenerative joint diseases, osteoporosis, periodontitis, and hyperthyroidism. Eur. Pat. App. No. -317-505-A discloses the use of 1-hydroxy-alkane-1,1-diphosphonic acid derivatives with azabicycloalkyl substitutions as useful for treating calcium metabolism disorders. The specific diseases mentioned include osteoporosis, hyperparathyroidism periodontitis, arthritis, neuritis, bursitis, tendinitis, fibrodysplasia, arteriosclerosis, Paget's disease, and osteodystrophia fibrosa. Australian Pat. App. No. 8781-453-A discloses the use of 2-heteroarylethane-1,1-diphosphonic acids as useful in the treatment of calcium metabolism disorders. Eur. Pat. App. No. -274-346-A discloses the use of 1-Azaheterocycloaminomethyl-1,1-diphosphonic acid derivatives to treat the same disorders. Eur. Pat. App. No. -272-208-A discloses the use of Azacycloalkyl-substituted 1-hydroxyalkane-1,1-diphosphonic acid compounds as useful also. Eur. Pat. App. No. -320-118-A discloses the use of phosphorus containing peptides useful as collagenase inhibitors and refers to periodontal disease.

As suggested above, it is known that bone resorption may be effectively treated with a variety of bisphosphonic acid derivatives. U.S. Pat. No. 4,621,077 ('077) describes the use of 4-amino-1-hydroxybutylidene-1,1 bisphosphonic acid ("ABP") in the treatment of bone loss that occurs in various bone diseases. The '077 patent teaches that the claimed bisphosphonic acid and its salt have inhibitory activity on bone reabsorption. Other phosphonate derivatives have been used to treat bone resorption. U.S. Pat. No. 5,002,937 describes novel diphosphonic acid compounds useful for treating calcium metabolism disorders. The '937 patent claims aminoalkane 1,1 diphosphonic acids in which the alkyl chain is interrupted by an oxygen atom (an ether link). European Patent Application No. 0 449 405 A2 broadly discloses the use of bisphosphonic acids for the treatment of calcium metabolism disorders. In particular, this European Application discloses the use of the calcium salt of 4-amino-1-hydroxybutylidene-1,1-bisphosphonic acid in the treatment of a multitude of bone diseases. U.S. Pat. Nos. 4,990,503 and 4,973,576 describe novel heterocyclic bisphosphonic acid derivatives that are potent bone resorption inhibitors. The art also suggests that the effects of bisphosphonates are variable and can produce opposite effects with different bisphosphonates or produce different biological responses at different concentrations with identical bisphosphonates. Fleish, H. Clin. Ortop., 217, 72–78 (1987).

U.S. Pat. No. 3,962,432 issued on Jun. 8, 1976 describes the use of 3-amino-1-hydroxypropane-1,1-disphosphonic acid in tarter control. U.S. Pat. No. 4,446,052 discloses the use of a calcium salt of 1-hydroxy-3-aminopropane-1,1-disphosphonic acid derivative to treat dental calculus and plaque. U.S. Pat. No. 4,877,603 teaches the use of geminal diphsophonate polymers in the treatment of plaque. Various other patents disclose the use of phosphonates as antigingivitis agents. These include U.S. Pat. Nos. 3,429,963; 4,102,993; 4,042,679; 4,100,270; 4,098,880; 4,123,512; and 4,138,477. Periodontal destruction in rice rats may be inhibited by bisphosphonates. Fleish, H. Clin. Ortop., 217, 72–78 (1987).

U.S. Pat. Nos. 4,711,880 and 4,639,338 disclose the preparation of 3-amino-1-hydroxypropane-1,1-diphosphonate pentahydrate.

The patent literature also describes the use of agents to induce new bone apposition in vivo. U.S. Pat. No. 4,816,437 discloses an alpha$_2$HS-Glycoprotein that induces bone apposition at a particular defective site. Bisphosphonates have been used to alter mineralization of the teeth. For example, the deposition of mineral crystallites in newly formed dentin is inhibited by 1-hydroxyethylidene-1,1-bisphosphonate. Beertsen, W., Neihof A., Everts, V. American J. Anat, 174, 83-103 (1985). These compounds may also affect collagen fibrilogenesis. Larsson, A. Calcif. Tissue Res., 16, 109-127 (1974); Ogawa Y, Adachi Y, Hong S, yagi, T. Calcif. Tissue Internat., 44, 46-60 (1989). Ultrastructural effects of disphosphonates on dental enamel has been studied as well. Simmelink, J. W., Adv. Dental Res. 1, 356-365 (1987). Prior to the instant invention, the art has not disclosed the use of a safe and highly effective bisphosphonate derivative to treat alveolar bone loss associated with periodontal disease in higher mammals. Treatment of this disease with anti-inflammatory agents and antibiotics only partially arrests progression of periodontitis.

Periodontal disease and periodontitis, as distinguished from other bone loss or calcium metabolism disorders, and the accompanying alveolar bone loss, is caused by aggressive bacterial or microbial buildup. It is generally assumed that plaque microorganisms and the products they produce are primarily responsible for periodontal disease. Riviere et al., Infection and Immunity, 59(10), 3377-3380 (1991). Spirochetes (non-flagellated, spiral bacteria) are major microbial components of dental plaque. Several other bacterial types may also be involved in periodontal disease progression including *Bacteroides melaninogenicus* (*Prevotella melaninogenica*), *Prevotella denticola*, *Prevotella loescheii*, *Bacteroides macacae*, *Porphyromonas gingivalis*, *Prevotella intermedia*, *Actinobacillus actinomycetemcomitans*, *Eikenella corrodens*, and *Wolinella recta*. Ebersole et al., Infection and Immunity, 59(10), 3351-3359 (1991). Active immunization with two of the well-established members of peridontpathic microbiota, P. gingivalis and P. intermedia as a possible alternative treatment has been found to induce a significant immune response but, the resultant antibodies did not prevent alveolar bone loss. Ebersole et al., Infection and Immunity, 59(10), 3351-3359 (1991). Periodontal disease is a universal disease which may affect over 95 percent of the world's population. S. Cripps, "Periodontal Disease: Recognition, Interception and Prevention", Quintessence Publishing Co. (1984). There is, therefore, a significant need for an effective treatment of alveolar bone loss associated with advanced peridontitis. There is an additional need to have an adequate adjunct therapy to prevent or treat bone loss associated with periodontal surgery. The instant claimed invention may advantageously be used as an adjunct therapy in conjunction with or after periodontal surgery to treat alveolar bone loss. One objective of the present invention is to combine a pharmaceutically effective amount of ABP or a pharmaceutically acceptable salt such as alendronate with known anti-inflammatory agents (for example, the analgesic and anti-inflammatory agent described in U.S. Pat. No. 4,677,132 or that described in U.S. Pat. No. 4,440,779) or known anti-microbial agents (for example, penicillin or erythromycin) to treat the overall progression of periodontal disease. Alternatively, ABP or its pharmaceutically acceptable salt such as alendronate can be used separately and/or concurrently with anti-microbial and/or anti-inflammatory agents to prevent, arrest, and treat periodontal disease.

SUMMARY OF THE INVENTION

The present invention provides a method of treating periodontal disease by administering an effective amount of 4-amino-1-hydroxybutylidene-1,1-bisphosphonic acid or a pharmaceutically acceptable salt such as the monosodium salt trihydrate to mammals, including humans. In addition, the claimed invention may be used as an adjunct therapy to periodontal surgery to prevent and treat bone loss associated with surgical manipulation. It is a further object of this invention to use an effective amount of ABP or its pharmaceutically acceptable salt such as alendronate in combination with an anti-inflammatory agent(s) or anti-microbial agent to treat and prevent both alveolar bone loss and inflammation associated with periodontal disease progression.

DETAILED DESCRIPTION OF THE INVENTION

The present invention provides a method of treatment of periodontal disease in mammals, including humans, using an effective amount of 4-amino-1-hydroxybutylidene-1,1-bisphosphonic acid or a pharmaceutically acceptable salt such as the monosodium salt trihydrate (alendronate):

ABP or alendronate may be prepared according to the process described in U.S. Pat. No. 5,019,651. A nonhuman primate system was chosen as a model system for studying the effects of alendronate on the treatment and prevention of periodontal disease. These primate models rather than the rat model are widely used to study periodontal disease. Periodontitis is induced in cynomolgus monkeys and generally produces a reproducible pattern of disease progression. This model system is well understood in the art to mimic or apply to adult humans in clinical, histological, microbiological, and immunological terms. In fact, cross-sectional microbial studies have established a solid relationship between ligature induced peridontitis in the non-human primate (Nhp) model and human periodontitis. Ebersole et al., Infection and Immunity, 59(10), 3351 (1991); Goodson et al., J. Clin. Periodontal., 57, 347-353 (1982); Haffajee et al., J. Clin. Periodontol., 10, 298-310 (1983); Holt et al., Science, 239, 55-57 (1988); and Nalbandian et al., J. Periodontal Res., 20, 154-164 (1987). See also Kiel et al., J. Periodontal Res., 18, 200-211 (1983); Kornman et al., J. Periodontal Res., 16, 363-371 (1981); manti et al., Infection and Immunity, 45, 172-179 (1984); McArthur et al., Infection and Immunity 57, 2313-2317 (1989); Nisengard et al., Immunol. Invest., 18, 225-237 (1989); and Slots et al., Infection and Immunity 23, 260-269 (1979). The squirrel monkey (Saimiri sciureus) has also been used as a Nhp model system for peridontitis in humans. Beem et al., Infection and Immunity 59(11), 4034-4041 (1991). A controlled study on primates exemplifies the claimed invention.

In addition, clinical studies on humans exemplify the unique advantages of the claimed invention. Double-blind, placebo-controlled parallel studies using twenty patients per treatment group were performed. 20 mg of alendronate (or placebo) may be given once daily for a six month period on patients who demonstrated alveolar bone loss of 30-50% and had pocket depths of at least 5 mm. Oral administration of two and one half (2.5) to eighty (80) milligrams daily for three to six months or longer may effectively treat periodontal disease (periodontitis) and alveolar bone loss. Efficacy is measured by examining alveolar bone height (dental x-rays), bone density (computerized radiography), and other factors including ginvival inflammation, plaque deposits, probing depths, and attachment levels.

The production of ABP or alendronate is first described followed by the detailed description of the treatment of periodontal disease in mammals (monkeys) with alendronate. Alendronate can readily be combined with known anti-inflammatory agents or known antibiotics to treat and prevent the overall progression of periodontal disease. These anti-inflammatory agents can be chosen from compounds such as those described in U.S. Pat. Nos. 4,677,132 or 4,440,779 or other suitable anti-inflammatory agent. The antibiotics can be chosen from penicillin (1000-1500 mg/day) or erythromycin or other suitable antibiotic. ABP or a pharmaceutically acceptable salt such as alendronate can be given separately in a suitable dosage of 0.25-50 milligrams daily or 5-40 milligrams daily to treat alveolar bone loss associated with periodontitis. In addition, ABP or alendronate in a pharmaceutically effective form and amount can be given separately and concurrently with a known anti-inflammatory or antibiotic.

The term "pharmaceutically effective amount" shall mean that amount of a drug or pharmaceutical agent that will elicit the biological or medical response of a tissue, system or animal that is being sought by a researcher or clinician. The compounds used in the present invention can be administered in such oral dosage forms as tablets, capsules (each of which includes substained release or timed release formulations), pills, powders, granules, elixirs, paste, tinctures, suspensions, syrups and emulsions. Likewise, they may also be administered in intravenous (bolus or infusion), intraperitoneal, subcutaneous or intramuscular form, all using forms well known to those of ordinary skill in the periodontal and pharmaceutical arts. An effective but non-toxic amount of the compound desired can be employed as an anti-alveolar bone loss agent.

The dosage regime utilizing the claimed method is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, dentist or veterinarian can readily determine and prescribed the effective amount of the drug required to prevent, counter or arrest the progress of the periodontal condition.

Oral dosages of the present invention, when used for the indicated effects, will range between 0.01 mg per kg of body weight per day (mg/kg/day) to about 1.0 mg/kg/day. Preferred dosages in mammals may range from 0.01 mg/kg to 0.8 mg/kg/day. The most preferred oral dosages in humans may range from daily total dosages of 2.5-50 mg/day over the effective treatment period. Oral dosages can be administered up to 80 mg/day. Intravenous injections or dosages of 0.005 to 0.40 mg/kg at two week intervals may also be administered in a preferred manner. The compounds of the invention may be administered in a single daily dose or a divided dose.

In the methods of the present invention, the bisphosphonate compounds herein described can form the major active ingredient. If a combination of the bisphosphonate and an anti-inflammatory agent or an antibiotic agent is used, then the bisphosphonates are the major active ingredients and the other components of the combination are the minor active ingredients. These compounds are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like and consistent with conventional pharmaceutical practices.

For instance, for oral administration in the form of a tablet or capsule, the active drug component can be combined with an oral, non-toxic, pharmaceutically acceptable inert carrier such as lactose, starch, sucrose, glucose, methyl cellulose, magnesium stearate, mannitol, sorbitol, and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture of active ingredient(s) and inert carrier materials. Suitable binders may include starch, gelatin, natural sugars such as glucose or beta-lactose, corn sweeteners, natural and synthetic gums such as acacia, tragacanth orsodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds used in the instant method may also be coupled with soluble polymers as targetable drug carriers. Such polymers can include polyvinylpyrrolidone, pyran copolymer, polyhydroxypropyl-methacrylamide and the like.

SYNTHESIS OF ABP AND ALENDRONATE

ABP or alendronate may be produced by bisphosphonating an aminoalkane carboxylic acid with phosphonating reactants in the presence of methanesulfonic acid, subsequent quenching with an aqueous hydrolysis mixture, maintaining the pH at 4 to 10, hydrolyzing the phosphorous intermediates produced in the quench, and recovering 4-aminohydroxybutylidene-1,1-bisphosphonic acid (ABP) or the various salts. The reaction is schematically represented in Scheme 1 as follows:

-continued
Scheme 1
$C_4H_{12}NNaO_7P_2 \cdot 3H_2O$

Various alternatives for the production of alendronate are provided in U.S. Pat. No. 5,019,651. Example 1 illustrates a synthesis of 4-amino-1-hydroxybutylidene-1,1-bisphosphonic acid (ABP) and its monosodium salt trihydrate.

EXAMPLE 1

Preparation of 4-amino-1-hydroxybutylidene-1,1-bisphosphonic acid (ABP) and its monosodium salt trihydrate Bisphosphonic Reaction Phase A 250 ml flask was fitted with a mechanical stirrer, a thermocouple, and addition funnel and a reflux condenser through which is circulated $-20°$ C. brine. The system was connected to a caustic scrubber which places a back pressure of 0.5-1 psig on the system. The system was flushed with nitrogen and charged with 20 g (0.19 mol) of aminobutyric acid, 160 ml of methansulfonic acid, and 32 g (0.39 mol) of phosphorous acid. For larger scale operations, the methanesulfonic acid can be charged first, followed by the 4-aminobutyric acid and phosphorous acid. Upon mixing, the heat of neutralization and solution increased the reaction temperature to 75° C. The suspension was aged for 15 minutes at 70°-75° C. and then cooled to 35° C. and phosphorous trichloride ($PCl_3$), 80 ml (0.92 mol) was added cautiously over twenty minutes. The reaction was then heated to 65° C. and run for a five hour period.

Quench; hydrolysis

The reaction mixture was quenched over 35 minutes by adding dropwise to a solution of 10 g of $Na_2HPO_4$ in one liter of water, at pH=7.0. The pH of the quench was maintained between 6.0 and 7.0 by simultaneously adding 25% sodium hydroxide and maintained below 25° C. by cooling with ice. Once the quench was complete, the pH was adjusted to 7.0 and the solution concentrated to 1080 ml by atmospheric distillation (100°-104° C.) over 3 hours. At this point, the reaction was subdivided into 2 parts, A and B.

A, being 630 ml, was concentrated further to 450 ml after adjusting the pH to 4.3. The solution was aged overnight at ambient temperature during which time the product crystallized. The suspension was aged at 0° C. for 2 hours then filtered, washed with 100 ml of cold water, 100 ml of 1:1 water/ethanol, and 100 ml of 100% ethanol and dried, yielding 20.5 g (56% yield).

B, being 450 ml, was treated by refluxing an additional 16 hours before adjusting the pH to 4.3 and concentrating to 300 ml. The product was isolated as above providing 16.5 g. (63% yield) of ABP. This example illustrates a synthesis of alendronate that minimizes the production of ABP dimers and phosphonates which are more difficult to hydrolyze and thus require longer hydrolysis times. The compound prepared in this manner may then be used to treat periodontal disease.

In Vivo Testing

Twenty-seven adult cynomolgus monkeys (*Macaca fascicularis*) with intact dentitions were obtained from a commercial supplier (Hazelton Research Animals, Inc.), or from in-house animals and placed on a soft chow diet. The animals were quarantined over an eight week period to ensure systemic health. Following this period, the animals were examined to acquire baseline data such as Plaque Index, Gingival Index, pocket measurements and intraoral radiographs. The method for obtaining a Plaque Index is described in Larsson, Calcif. Tissue Res. 16, 109-127 (1974). The method for obtaining a Gingival Index is described in Ogawa et al., Calcif. Tissue Internat., 44, 46-60 (1989). Pocket depth is measured from the gingival margin to the base of the pocket by the same examiner to ensure consistency. A Michigan periodontal probe was used to conduct this analysis.

A standardized radiographic procedure that utilized custom made acrylic occlusal registrations created the intraoral radiographs used in this invention. This procedure is described in Simmelink, J. W., Adv. Dental Res., 1, 356-365 (1987). The radiographic technique required modification of a beam-guiding, field-limiting intraoral instrument to produce repeatable superimposed radiographic images. The radiographs obtained were then analyzed for quantitative changes in bone density using a computer assisted densitometric analysis (CADIA) system. This computerized approach is described in Jung A, et al., Cancer, 48, 1922-1925 (1985). This system objectively determines bone density. The system operator inputs the film alignment data and expresses the bone density change in CADIA units. The latter are a function of the magnitude of density change and the area of this change. Steffensen et al. describes this process. J. Periodont. Res., 26, 107-113 (1991). This radiographic technique is well understood in the art to accurately measure loss of bone density. For example, see Ebersole et al., Infection and Immunity 59(11), 3351-3359 (1991).

The effect on mandibular molars was evaluated clinically. Six sites per tooth were scored for clinical probing pocket depth. Four sites per tooth were scored for GI and PlI. Experimental sites were limited to the mandible because standard radiographs are not readily used in the maxilla.

The adult cynomolgus monkeys were divided into three groups to receive one of three treatment agents. Two concentrations of alendronate and a saline placebo were administered. The administered concentrations were 0.05 mg/kg to 0.25 mg/kg. The concentrations were prepared prior to administration of the treatment drug. The two concentrations of alendronate and the saline placebo were injected in the saphenous vein (intravenously) of the lower leg every two weeks (at a two week interval) for a sixteen week period. The monkeys were anesthetized with ketamine (10 mg/kg) and acepromazine (0.5 mg/kg) for each treatment injection and during clinical and radiographic examinations.

One week after the treatment compounds were administered the mandibular right molars and the premolars were ligated with 3-0 silk sutures at the cementoenamel junction to initiate peridontitis. Two weeks later the ligated teeth were deliberately infected with *Porphyromonas gingivalis* obtained from cynomolgus monkeys. These bacterial colonies were scraped from the surface of the culture medium with a sterile curette and applied to the ligatures. This procedure was repeated two weeks later. The purpose of this treatment was to induce and ensure a severe etiolic disturbance in the periodontium. It is necessary to check the animals on a routine basis (weekly) to replace ligatures when necessary.

Periodontal disease progression was monitored by clinical measurements and radiographs. These experiments were repeated eight and sixteen weeks after ligation to determine the effect of the various concentrations of alendronate and the saline placebo. Table 1 presents a summary of the experimental procedures followed:

TABLE 1

| Experimental Protocol | | | | | | | | | | | | |
|---|---|---|---|---|---|---|---|---|---|---|---|---|
| | Time Period in Weeks | | | | | | | | | | | |
| | -1 | 0 | 1 | 3 | 5 | 7 | 8 | 9 | 11 | 13 | 15 | 16 |
| Clinical & Radiographic | x | | | | | | x | | | | | x |
| Ligatures Placed | | x | | | | | | | | | | |
| P. gingivalis | | | | x | x | | | | | | | |
| Administration of Treament | x | | x | x | x | x | | | x | x | x | x |

Figure 1:
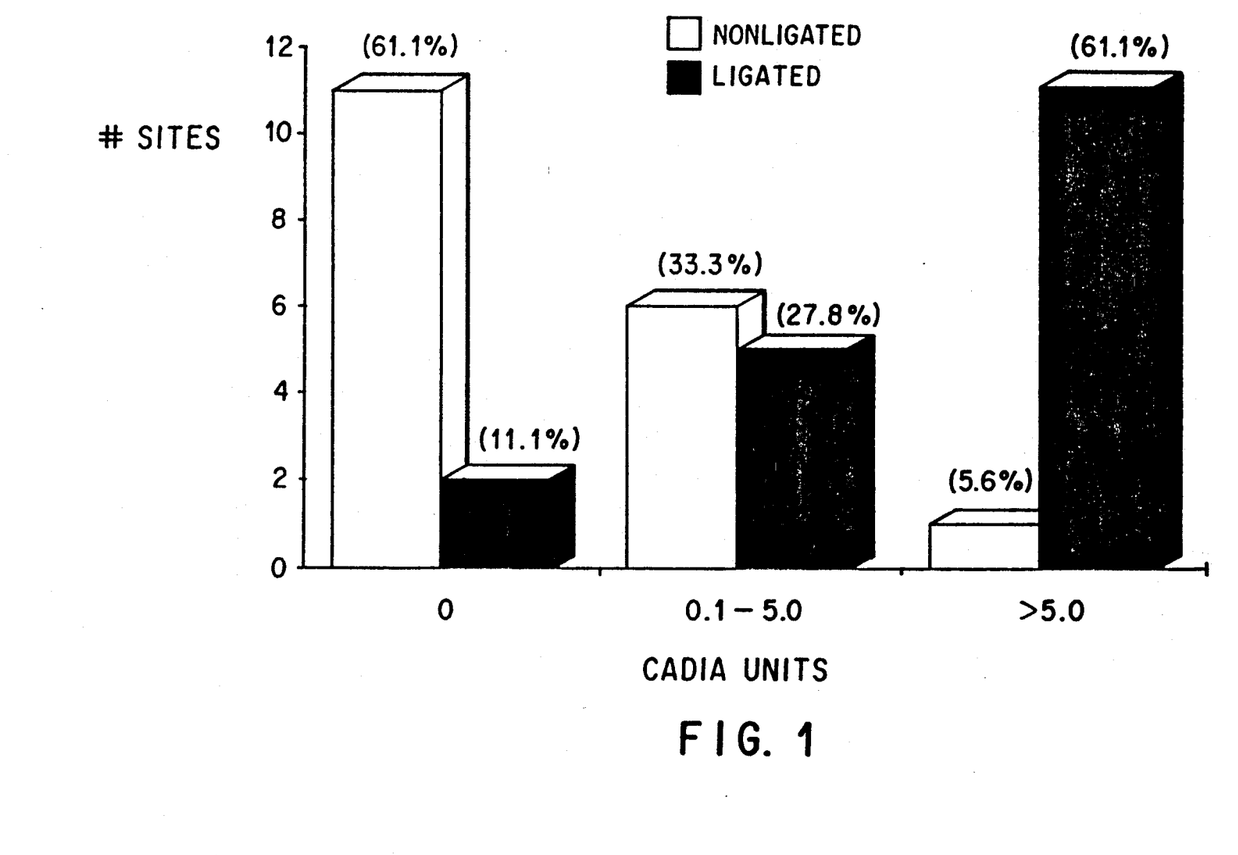
Figure 2:
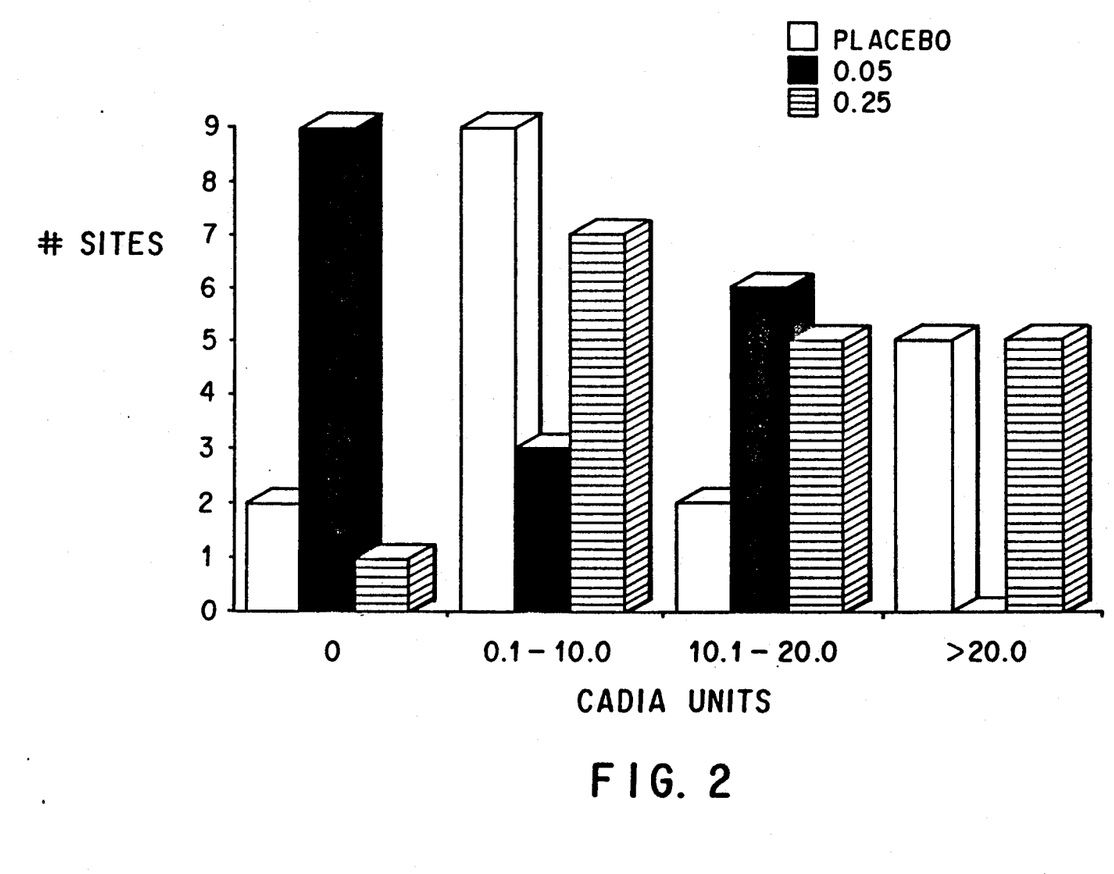
Figure 3:
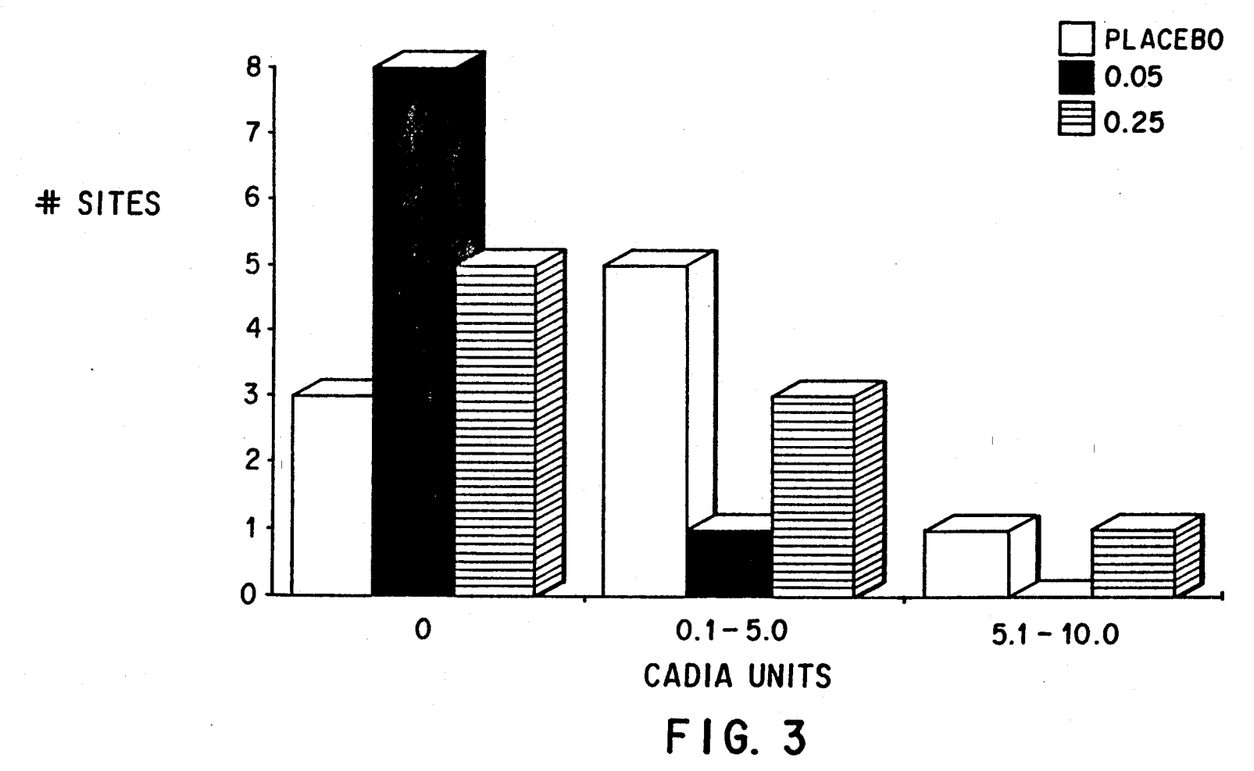

The clinical measurements were then analyzed statistically with the paired t-test and with analysis of variance. The radiographic data were also compared using analysis of variance. The change in radiographic bone density after application of the various treatments expressed in CADIA Units is shown in FIGS. 1-3. FIG. 1 shows the effect of ligation on density loss in the placebo animals.

FIG. 2 demonstrates the density loss in Interproximals and FIG. 3 exhibits the density loss in Furcations.

In the placebo group of nine animals, 11 of 18 or 61.1% of the interproximal sites of nonligated teeth did not lose bone density during the sixteen week study period. Interproximal is defined as the space between adjoining teeth. A loss of bone density did occur in 16 of 18 sites or 88.9% of the ligated teeth. This demonstrates the effectiveness and reproducibility of the model system for inducing periodontal disease and loss of bone density.

EXAMPLE 2

Alendronate at a concentration of 0.05 mg/kg was injected intravenously into the saphenous vein of the lower leg of one group (nine animals) of the three total groups of test primates. The animals were anesthetized with ketamine (10 mg/kg) and acepromazine (0.5 mg/kg) at each injection of the alendronate. One week later, the mandibular right molars and the pre-molars were ligated with 3-0 silk sutures at the cementenamel junction to induce peridontitis. Two weeks later, the ligated teeth were infected with the bacterium *Porphyromonas gingivalis* by scraping the culture medium with a sterile curette and application to the surface of the ligatures. After another two weeks, the animals were reinfested with the active *P. gingivalis* bacterium. The monkeys were checked weekly and ligatures replaced if necessary. Clinical examinations and measurements and radiographs were performed eight and sixteen weeks after the initial ligation to determine the effect of alendronate on peridontitis progression. Eighteen interproximal sites (two per animal) were assessed radiographically. A similar procedure was followed for the saline placebo and for alendronate at a concentration of 0.25 mg/kg. As FIG. 2 demonstrates, alendronate at a concentration of 0.05 mg/kg had a significant effect on alveolar bone loss in the infected animals.

Nine of the eighteen interproximal experimental sites had no loss in bone density after treatment with the 0.05 mg/kg of alendronate. The bone density loss in this group was less than either the placebo ($p<0.05$) or the 0.25 mg/kg groups.

Nine furcation sites (1 per animal) were also evaluated for each treatment group. A furcation is the anatomical area of a multirooted tooth where the roots divide. As FIG. 3 demonstrates, the results of bone density loss(or lack thereof) parallel those of the interproximal region(s).

Eight of the nine furcation sites in the 0.05 mg/kg concentration group did not lose bone density. The placebo group and the higher concentration of alendronate (0.25 mg/kg) did have bone loss in the furcation sites. Similar results were achieved on a second group of nine animals. The results demonstrate that alendronate (0.5 mg/kg given intravenously at two week intervals) has a significant inhibitory effect on bone loss associated with periodontitis and periodontal disease progression.

The compounds disclosed in the instant invention and used according to the methods claimed in the instant invention may be administered according to standard pharmaceutical practice. The above examples are not intended to limit or otherwise restrict the application of the instant invention. Typical pharmaceutical formulations and carriers may be used to administer or deliver the active bisphosphonic acid or its suitable salt or hydrate alone or in combination with known anti-inflammatory agents or known antibiotics.

The compounds used in the instant invention may be administered orally (0.25-80 mg/day or 0.01 to 0.8 mg/kg/day for six months or longer as necessary to arrest peridontitis), intravenously (0.005-0.40 mg/kg) or topically (directly applied to an inflamed area in the tooth and gum) to treat alveolar bone loss associated with peridontitis. The compounds may also be orally administered in dosages ranging from 0.25-80 mg/day ABP and its pharmaceutically acceptable salts which are readily soluble in the bloodstream may be combined with inert carriers such as sugars (glucose, lactose, or saccharose), starch or starch derivatives, cellulose or cellulose derivatives, typical gums or gels, inert fatty acids and their salts or other typical carriers or formulations.

Delivery systems may include operculated capsules or effervescent granules for an oral treatment regime or solutions suitable for intravenous injection. The capsule formulations may contain, in addition to the active ingredient(s) (ABP or its pharmaceutically acceptable salt if given as the sole active ingredient or ABP or its pharmaceutically acceptable salt in combination with a known anti-inflammatory agent and/or a known antibiotic such as penicillin), lactose, hydrolyzed starch, talcum or magnesium stearate in typical and pharmaceutically acceptable ratios. The effervescent granulates in addition to the active ingredient(s) may contain anhydrous sodium carbonate, sodium bicarbonate, anhydrous citric acid, sodium saccharinate, saccharose, dehydrated lemon juice in typical pharmaceutical ratios. Formulations suitable for intravenous delivery may contain the active ingredient(s) and typical buffering agents and salts dissolved in the appropriate quantity of aqueous solution. For example, 0.5 mgs of ABP or its salt may be combined with 0.25 mg of sodium hydroxide, 8.4 mgs of sodium chloride and dissolved in 1.0 ml of purified water.

While the invention has been described and illustrated in reference to certain preferred embodiments thereof, those skilled in the art will appreciate that various changes, modification and substitutions can be made therein without departing from the spirit and scope of the invention. For example, effective dosages other than the preferred doses as set forth hereinabove may be applicable as a consequence of variations in the responsiveness of the mammal or human being treated for periodontal disease. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended that the invention be limited only by the scope of the claims which follow and that such claims be interpreted as broadly as is reasonable.

What is claimed is:

1. A method of treating alveolar bone loss associated with periodontitis in human and non-human primate patients afflicted therewith comprising administering an oral dosage of 0.25-80 mg/day or an intravenous dosage of 0.005-0.40 mg/kg/2 week interval to said patient to treat alveolar bone loss associated with periodontitis of alendronate of the formula:

2. A method of treating alveolar bone loss according to claim 1 comprising administering an oral dosage of alendronate in the 0.25-80 mg/day range or in the 0.01 mg/kg/day to 0.8 mg/kg/day range.

3. A method of treating alveolar bone loss according to claim 1 comprising administering an intraveneous dosage of 0.005 to 0.40 mg/kg at a two week interval.

4. A method of treating alveolar bone loss according to claim 1 comprising administering 4-amino-1-hydroxybutylidene-1,1-bisphosphonic acid (ABP) trihydrate or a pharmaceutically acceptable salt thereof with a pharmaceutically acceptable carrier.

5. A method of treating alveolar bone loss in mammals, including humans, comprising administering an effective amount of 4-amino-1-hydroxybutylidene-1,1-bisphosphonic acid (ABP) or a pharmaceutically acceptable salt, excluding a calcium salt, thereof.

6. A method of treating alveolar bone loss according to claim 5 comprising administering an effective amount of alendronate.

7. A method of treating alveolar bone loss according to claim 6 comprising administering an oral dosage of alendronate in the 0.25-80 mg/day range or in the 0.01 mg/kg/day to 0.8 mg/kg/day range.

8. A method of treating alveolar bone loss according to claim 6 comprising administering an intravenous dosage of 0.005 to 0.40 mg/kg at a two week interval.

9. A method of treating alveolar bone loss associated with periodontitis in human and non-human primates afflicted therewith comprising administering 4-amino-1-hydroxybutylidene-1,1-bisphosphonic acid monosodium salt trihydrate (alendronate) with a pharmaceutically acceptable carrier.

10. A method of treating alveolar bone loss associated with periodontitis in human and non-human primates afflicted therewith, comprising administering an effective amount of ABP according to claim 1 as an adjunct therapy to periodontal surgery.

* * * * *